US012564394B2

(12) United States Patent
Chen et al.

(10) Patent No.: US 12,564,394 B2
(45) Date of Patent: Mar. 3, 2026

(54) OCCLUDER AND OCCLUDING SYSTEM

(71) Applicant: Lifetech Scientific (Shenzhen) Co. Ltd., Guangdong (CN)

(72) Inventors: XianMiao Chen, Shenzhen (CN); XiaoYue Lei, Shenzhen (CN); DongYang Zhao, Shenzhen (CN)

(73) Assignee: Lifetech Scientific (Shenzhen) Co. Ltd., Guangdong (CN)

( * ) Notice: Subject to any disclaimer, the term of this patent is extended or adjusted under 35 U.S.C. 154(b) by 11 days.

(21) Appl. No.: 18/724,267

(22) PCT Filed: Oct. 20, 2022

(86) PCT No.: PCT/CN2022/126333
§ 371 (c)(1),
(2) Date: Jun. 26, 2024

(87) PCT Pub. No.: WO2023/124440
PCT Pub. Date: Jul. 6, 2023

(65) Prior Publication Data
US 2025/0090153 A1 Mar. 20, 2025

(30) Foreign Application Priority Data
Dec. 30, 2021 (CN) .......................... 202111650534.5

(51) Int. Cl.
*A61B 17/00* (2006.01)
(52) U.S. Cl.
CPC .... *A61B 17/0057* (2013.01); *A61B 17/00234* (2013.01); *A61B 2017/00243* (2013.01);
(Continued)
(58) Field of Classification Search
CPC .......... A61B 17/00234; A61B 17/0057; A61B 2017/00243; A61B 2017/00305;
(Continued)

(56) References Cited

U.S. PATENT DOCUMENTS

| | | | |
|---|---|---|---|
| 5,087,246 A | 2/1992 | Bard | |
| 2007/0208376 A1 | 9/2007 | Meng | |

(Continued)

FOREIGN PATENT DOCUMENTS

| | | |
|---|---|---|
| CN | 204181743 U | 3/2015 |
| CN | 105455922 A | 4/2016 |
| CN | 106344100 A | 1/2017 |

OTHER PUBLICATIONS

International Search Report dated Dec. 7, 2022 for corresponding PCT Application No. PCT/CN2022/126333.

(Continued)

*Primary Examiner* — Ryan J. Severson
(74) *Attorney, Agent, or Firm* — Raymond Sun

(57) ABSTRACT

The present invention is applicable to the technical field of interventional medical devices and provides an occluder and an occluding system having the occluder. The occluder includes a woven main body, where the woven main body is formed by shaping a woven mesh tube formed by weaving woven wires having a shape memory function. The woven main body is provided with a shrinkage deformation resistance reduction structure that reduces a resistance of the woven main body entering a pipe; the shrinkage deformation resistance reduction structure reduces the resistance of the woven main body entering the pipe by reducing the contact area between the woven main body and an inner wall of the pipe during radial shrinkage deformation of the woven main body entering the pipe so that the occluder may smoothly and successfully enter a pipe of a delivery sheath, thereby greatly reducing the operation difficulty and risk caused by unsmooth entry of the occluder into the delivery sheath.

13 Claims, 13 Drawing Sheets

100'

(52) U.S. Cl.
   CPC ............... *A61B 2017/00305* (2013.01); *A61B 2017/00592* (2013.01); *A61B 2017/00606* (2013.01); *A61B 2017/00623* (2013.01); *A61B 2017/00862* (2013.01); *A61B 2017/00867* (2013.01)

(58) Field of Classification Search
   CPC ........... A61B 2017/00592; A61B 2017/00601; A61B 2017/00606; A61B 2017/0061; A61B 2017/00623; A61B 2017/00862; A61B 2017/00867
   See application file for complete search history.

(56) References Cited

U.S. PATENT DOCUMENTS

| | | |
|---|---|---|
| 2011/0270174 A1 | 11/2011 | Lifetech |
| 2014/0173878 A1 | 6/2014 | Cook |

OTHER PUBLICATIONS

Search Report dated Mar. 13, 2025 in corresponding European Appl. No. EP 22 91 3703.

100'

401a

A—A

100

10b

11b

12b

20

401b

401c

11d

12d

13d

A

10d

B

C

401d

A

401d

B

401d

C

10e

11e

12e

13e

A

B

C

D

100

401g                    401g

401g

401g

401h

10h

10i

401i

Waist portion       Transparent pipe

Recess at waist portion

OCCLUDER AND OCCLUDING SYSTEM

TECHNICAL FIELD

The present invention belongs to the technical field of interventional medical devices, and particularly relates to an occluder and an occluding system having the occluder.

BACKGROUND ART

Atrial septal defect (ASD) is a common congenital cardiac malformation in clinical practice. It is an abnormality of the original atrial septum during embryonic development, resulting in an opening between the left and right atria. It is typically treated with an ASD occluder. As shown in FIG. 1, the existing occluder 100' is commonly formed by weaving woven wires. The woven occluder is compact in weaving and the constraining force between the woven wires is large, so that the force required to deform the occluder 100' increases. Therefore, the resistance of the occluder 100' entering a sheath is increased, making it difficult to adapt to a small sheath. When it is required to deliver the occluder 100' through a small sheath, for example, as shown in FIG. 2, a delivery sheath 50' is usually small in size (such as a delivery sheath with an inner diameter of 6F or less) when performing an interventional operation on children. At this time, if the resistance of entering the sheath is too high, it will increase the difficulty and risk of the operation, and even endanger the safety of patients.

SUMMARY OF THE INVENTION

It is an object of the present invention to provide an occluder to solve the problem that the occluder of the related art has a great resistance to entering a sheath, increasing the difficulty and risk of the operation.

The present invention is realized as follows. An occluder is provided, including:

a woven main body, where the woven main body is formed by shaping a woven mesh tube formed by weaving woven wires having a shape memory function;

the woven main body is provided with a shrinkage deformation resistance reduction structure that reduces a resistance of the woven main body entering a pipe; the shrinkage deformation resistance reduction structure reduces the resistance of the woven main body entering the pipe by reducing the contact area between the woven main body and an inner wall of the pipe during radial shrinkage deformation of the woven main body entering the sheath.

Specifically, the shrinkage deformation resistance reduction structure includes a recess provided on the woven main body, and the recess is recessed toward an inner side of the woven main body.

In some embodiments, at least one recess is provided, and the recess penetrates a proximal end and a distal end of the woven main body.

In some embodiments, the woven main body includes a distal disc and a shrinkage portion connected to the distal disc, and the radial cross-sectional dimension of the shrinkage portion is smaller than the radial cross-sectional dimension of the distal disc; the recess is close to a transitional connection of the distal disc and the shrinkage portion;

or, the recess is provided at the transitional connection of the distal disc and the shrinkage portion.

In some embodiments, the recesses are distributed along a side wall of the woven mesh tube in a spiral trajectory.

In some embodiments, the woven main body includes a distal disc, a proximal disc, and a waist portion connected between the proximal disc and the distal disc; disc surface dimensions of the distal disc and the proximal disc are greater than the radial cross-sectional dimension of the waist portion; a plurality of recesses are provided, and the plurality of recesses are distributed on the woven main body at intervals and have different depths; the depth of the recess on the proximal disc close to the longitudinal central axis of the proximal disc is less than the depth of the recess away from the longitudinal central axis of the proximal disc, and the depth of the recess on the distal disc close to the longitudinal central axis of the distal disc is less than the depth of the recess away from the longitudinal central axis of the distal disc.

In some embodiments, the occluder includes a proximal bolt head provided at a proximal end of the woven main body; the recess is provided at an end portion of the proximal end of the woven main body and is provided opposite the proximal bolt head.

In other embodiments, an even number of the recesses are provided, and the even number of the recesses are provided in pairs on a side wall of the woven mesh tube; any pair of the recesses are provided symmetrically about the central axis of the woven mesh tube.

In some embodiments, a plurality of recesses is provided, each of the recesses penetrates the woven mesh tube along an axial direction, and the plurality of recesses is asymmetrically provided on a side wall of the woven mesh tube.

In other embodiments, a plurality of recesses is provided, and the plurality of recesses is distributed on the woven mesh tube at intervals in a mesh point shape.

In other embodiments, the present invention also provides an occluding system including any of the above-mentioned occluder.

The present invention provides an occluder, and the woven main body of the occluder is provided with the shrinkage deformation resistance reduction structure. The shrinkage deformation resistance reduction structure reduces the resistance of the woven main body entering the pipe by reducing the contact area between the woven main body and the inner wall of the pipe of the delivery sheath during radial shrinkage deformation of the woven main body entering the pipe so that the woven main body of the occluder may successfully enter the pipe of the delivery sheath or the like, and blockage, jamming, or the like when the occluder enters the pipe of the delivery sheath or the like may be reduced or avoided, thereby reducing the difficulty and risk of the operation.

DETAILED DESCRIPTION OF THE INVENTION

In order to make the objects, technical solutions, and advantages of the present invention clearer and more understandable, the present invention is further described in detail below in conjunction with the accompanying drawings and embodiments. It should be understood that the specific embodiments described herein are illustrative only and are not intended to limit the present invention.

It should be noted that when an element is referred to as being "fixed" or "provided" on another element, it may be directly on the other element or intervening elements may be present. When an element is referred to as being "connected" to another element, it may be directly connected to the other element or intervening elements may be present.

It should also be noted that the terms left, right, up, down, etc. in the embodiment are merely relative concepts or references to the normal use of the product, and should not be construed as limiting.

In the field of interventional medical devices, "distal" is defined as the end away from the operator during the procedure and "proximal" is defined as the end close to the operator during the procedure. "Axial" refers to a direction parallel to a line connecting a center of a distal end and a center of a proximal end of a medical device, and "radial" refers to a direction perpendicular to the above-mentioned axial direction.

Figure 1:
FIG. 1 is a schematic diagram of an occluder of the related art in a natural state according to the present invention.
Figure 1:
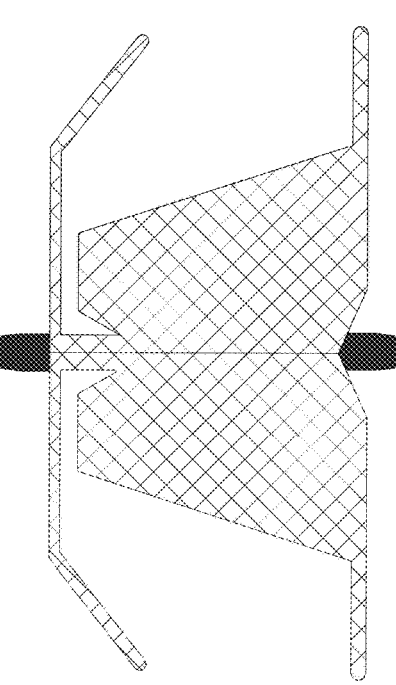
Figure 2:
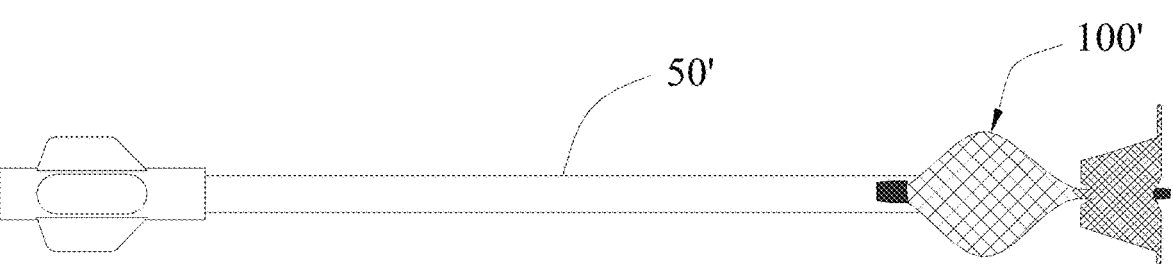
FIG. 2 is a schematic diagram of an occluder of the related art entering a sheath according to the present invention.
Figure 3:
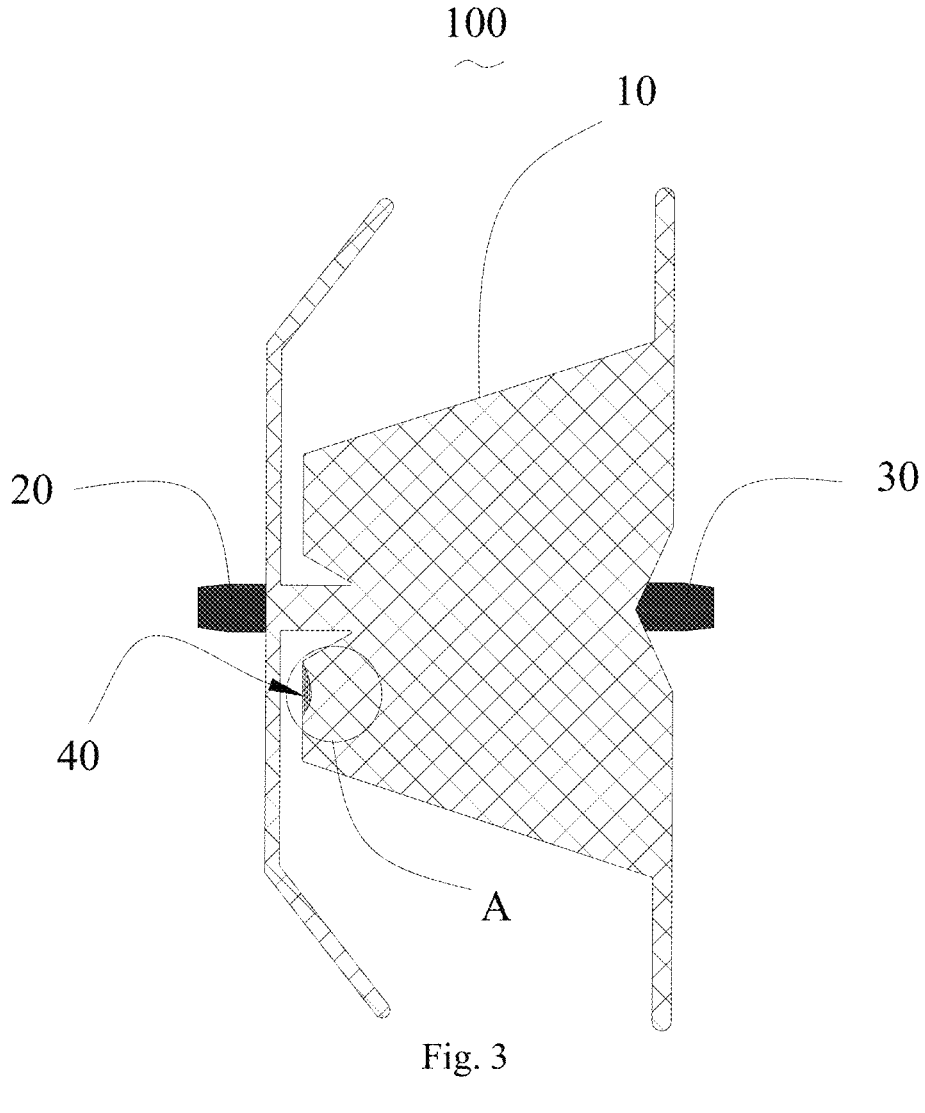
FIG. 3 is a schematic diagram of a dual disc-shaped occluder according to an embodiment of the present invention.

As shown in FIG. 3, a dual disc-shaped occluder 100 according to an embodiment of the present invention includes a woven main body 10, a proximal bolt head 20, and a distal sealing head 30. The woven main body 10 is formed by shaping a woven mesh tube formed by weaving woven wires having a shape memory function, such as nickel-titanium alloy metal wires, and has a proximal free end and a distal free end. The proximal bolt head 20 is located at a proximal end of the woven main body 10 and is configured to assemble and fix the proximal free end of the woven main body 10. The distal sealing head 30 is located at a distal end of the woven main body 10 and is configured to assemble and fix the distal free end of the woven main body 10. The woven main body 10 is provided with a shrinkage deformation resistance reduction structure 40 to reduce the resistance of the woven main body 10 entering a pipe; for example, reducing the resistance of the woven main body 10 entering a pipe of a delivery sheath, or reducing resistances of end portions of free ends of the woven main body 10 entering the proximal bolt head 20 and the distal sealing head 30. The shrinkage deformation resistance reduction structure 40 reduces the resistance of the woven main body entering the pipe by reducing a contact area between the woven main body 10 and an inner wall of the pipe during radial shrinkage deformation of the woven main body 10 entering the pipe.

Figure 3A:
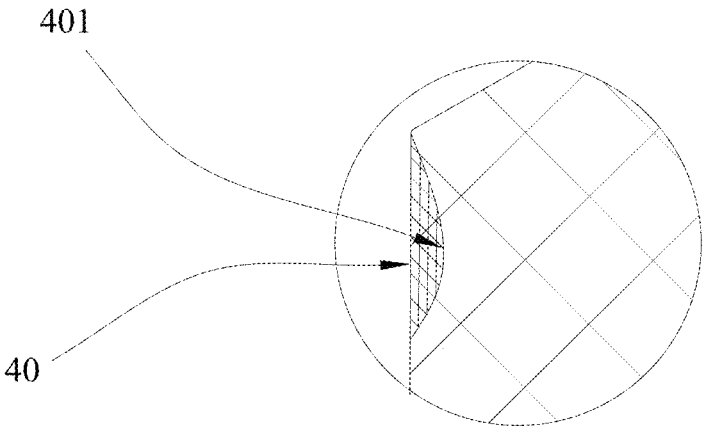
FIG. 3a is an enlarged schematic diagram at A of FIG. 3.

Referring to FIGS. 3 and 3a, the shrinkage deformation resistance reduction structure 40 provided in this embodiment includes a recess 401 provided on the woven main body 10, and the recess 401 is recessed toward an inner side of the woven main body 10. The recess 401 may be a recess of any shape, such as an arcuate recess, a V-shaped recess, or a rectangular recess, or a recess of an irregular shape, as long as it is recessed toward the inner side of the woven main body 10 with respect to an outer wall of the woven main body 10. The woven main body 10 needs to be shrunk when entering a narrow pipe space such as the delivery sheath, resulting in a large radial pressure. At this time, there will be an abutment against the inner wall of the pipe of the delivery sheath, and if an abutment stress is too large, the delivery of the occluder will be blocked. The recess 401 is provided to enable the woven main body 10 to distribute a part of the stress toward the inner side of the woven main body 10 when the woven main body 10 undergoes shrinkage deformation, thereby reducing the contact with the inner wall of the pipe of the delivery sheath, namely, reducing the radial stress abutting against the inner wall of the pipe so that the woven main body 10 may enter the pipe such as the delivery sheath more smoothly, avoiding blockage, jamming, or the like when entering the sheath and reducing the operation difficulty and risk.

Figures 4, 5:
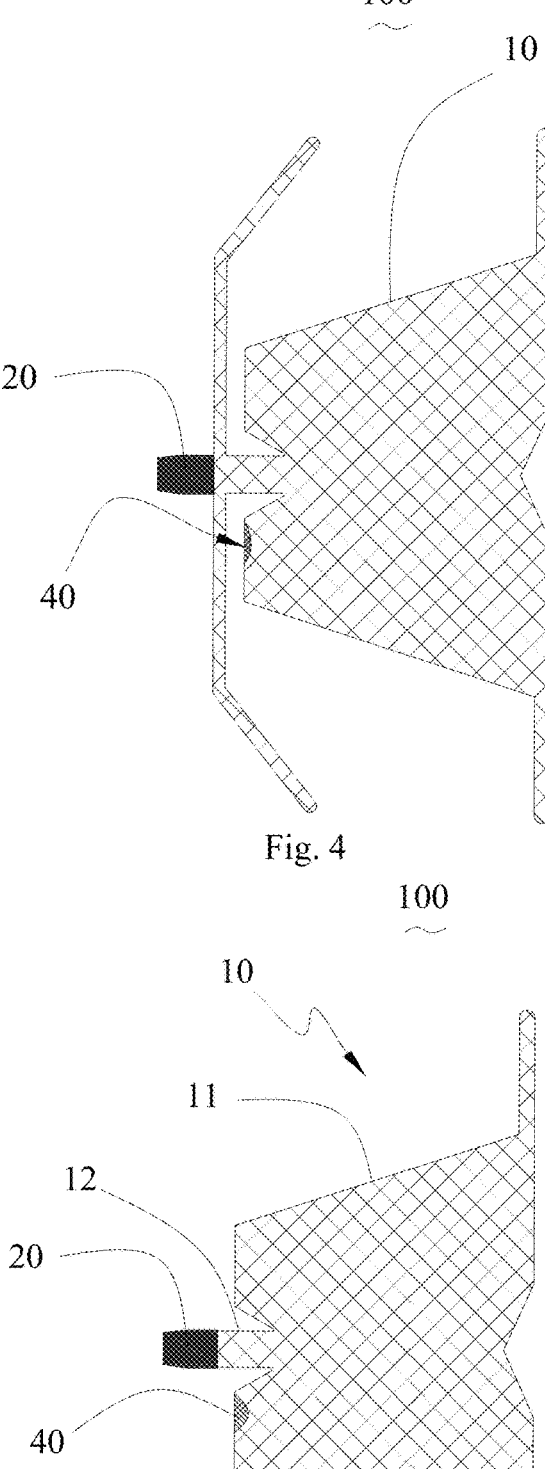
FIG. 4 is a schematic diagram of an occluder without a distal sealing head at a distal end according to an embodiment of the present invention.
FIG. 5 is a schematic diagram of a single disc-shaped occluder according to an embodiment of the present invention.

As shown in FIG. 4, in other embodiments, the occluder 100 may be provided with only the woven main body 10 and the proximal bolt head 20, with the shrinkage deformation resistance reduction structure 40 being provided on the woven main body 10. Namely, in this embodiment, the distal end of the woven main body 10 of the occluder 100 may be gathered and fixed by the weaving, winding, and bounding of the woven wires of the woven main body 10 itself, achieving the function of bundling and fixing the distal end. In other words, the occluder in the embodiment is not provided with a distal sealing head. Alternatively, the woven wires at the distal end of the occluder 100 may be bundled and fixed by welding, achieving the function of bundling and fixing the distal end.

As shown in FIG. 5, in other embodiments, unlike the dual disc-shaped occluder of the foregoing embodiments, the woven main body 10 of the occluder 100 is single disc-shaped, namely, the woven main body 10 includes only a distal disc 11, a waist portion 12, and the proximal bolt head 20, and the shrinkage deformation resistance reduction structure 40 is provided on the distal disc 11. The shrinkage deformation resistance reduction structure 40 is provided on the distal disc 11 so that the resistance of the occluder 100 entering the sheath is reduced by reducing the contact area with the inner wall of the pipe during radial shrinkage deformation of the occluder 100 entering the pipe of the sheath.

Figure 6:
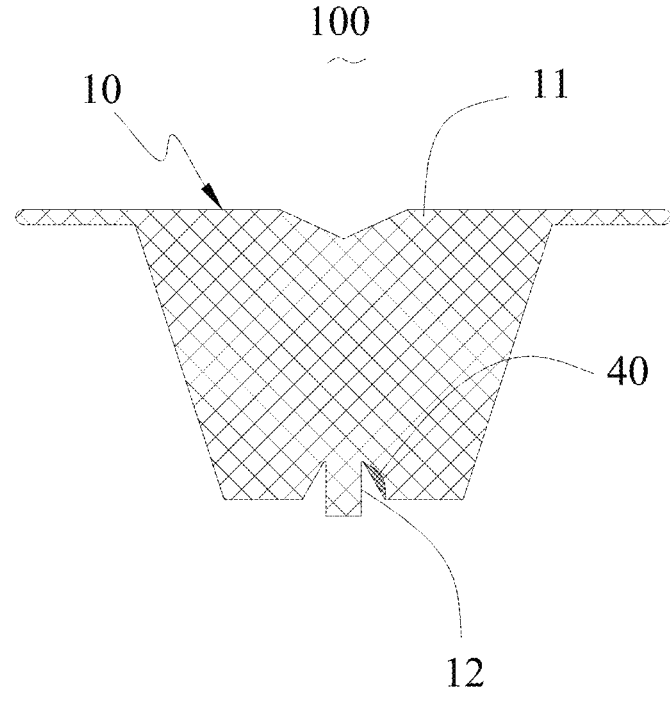
FIG. 6 is a schematic diagram of an occluder without a proximal bolt head and a distal sealing head according to an embodiment of the present invention.

As shown in FIG. 6, in other embodiments, the occluder 100 may only include the woven main body 10. The woven main body 10 includes the distal disc 11 and the waist portion 12, and the shrinkage deformation resistance reduction structure 40 is provided on the distal disc 11 of the woven main body 10, namely, in this embodiment, the occluder 100 is not provided with a proximal bolt head and a distal sealing head, and the proximal end and the distal end of the occluder 100 may be bundled by weaving and winding of the woven wires or may be bundled by welding.

The specific arrangement of the shrinkage deformation resistance reduction structure 40 on the occluder 100 is exemplified as follows.

Embodiment 1

Figure 7:
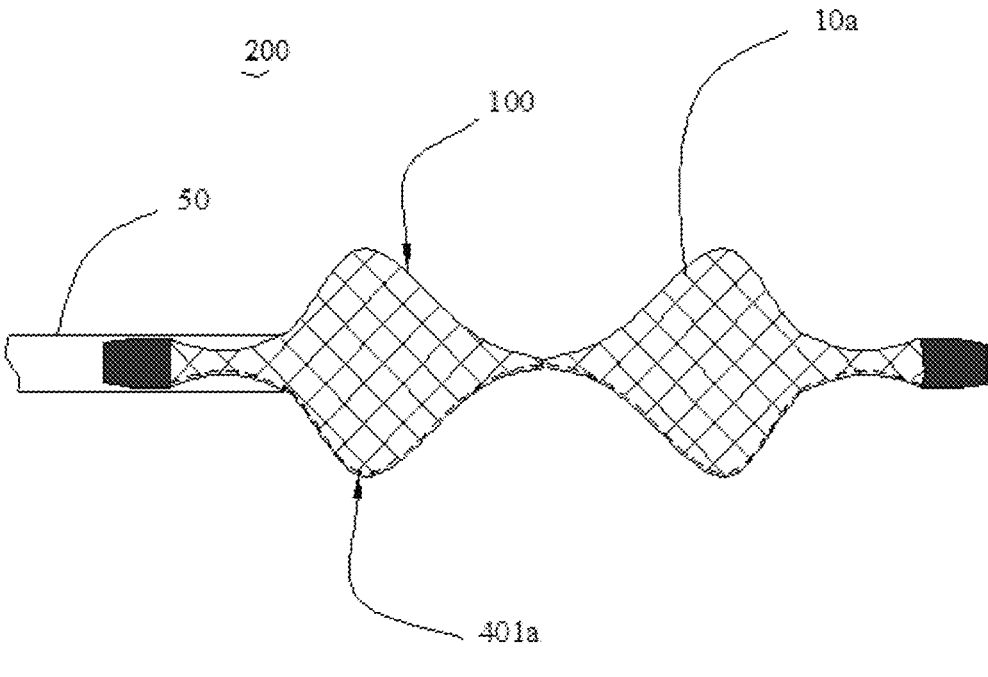
FIG. 7 is a schematic diagram of an occluder in a stretched state according to embodiment 1 of the present invention.
Figure 8:
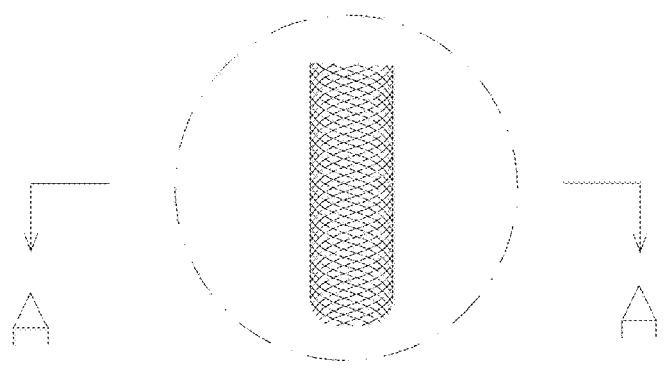
FIG. 8 is a schematic diagram of a woven mesh tube according to embodiment 1 of the present invention.
Figure 9:
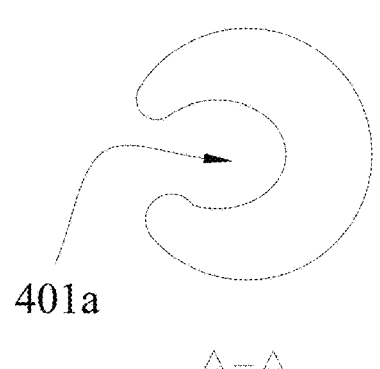
FIG. 9 is a schematic cross-sectional diagram of a woven mesh tube of FIG. 8 taken along the line A-A.

Referring to FIGS. 7 to 9, in this embodiment, as shown in FIG. 7, only one recess 401a is provided, and the recess 401a penetrates a proximal end and a distal end of a woven main body 10a, namely, the recess 401a is provided on a side wall of the woven main body 10a in the shape of a groove extending from the proximal end to the distal end of the woven main body 10a. Refer to FIG. 8, which is a schematic diagram of a woven mesh tube before being shaped into the woven main body 10a. The woven mesh tube is generally cylindrical before being shaped into the woven main body 10a shown in FIG. 7. At this time, the recess 401a may be formed on the side wall of the woven mesh tube using an auxiliary clamp, and the cross-section of the woven mesh tube presents a concave shape as shown in FIG. 9. Of course, a plurality of recesses 401a may also be provided in this embodiment, and the plurality of recesses 401a all penetrate the proximal end and the distal end of the woven main body 10a, namely, the plurality of recesses 401a are provided in parallel.

In some specific embodiments, a specific method for manufacturing the recess 401a may be performed as follows. The whole cylindrical woven mesh tube as shown in FIG. 8 is bounded using a thin copper wire so that a side wall of the whole cylindrical woven mesh tube as shown in FIG. 8 is recessed to form a groove penetrating the proximal end and the distal end of the woven mesh tube, and the cross-section thereof is as shown in FIG. 9. The woven mesh tube is pressed due to binding so that an area of an internal cavity is reduced. Then, the woven mesh tube is shaped to form the woven main body 10a. After the woven main body 10a is shaped, the bounding of the thin copper wire is released. When the occluder 100 enters a delivery sheath 50 as shown in FIG. 7 to form an occluding system 200, since the whole woven main body 10a is recessed, the woven main body 10a is compressed and deformed. Since the recess 401a of the woven main body 10a is provided, the recess 401a of the woven main body 10a is pressed to an inner side of the woven main body 10a so that a contact area between the woven main body 10a and an inner wall of the delivery sheath 50 may be relatively reduced, and a positive pressure between the woven main body 10a and the delivery sheath 50 may be reduced. Therefore, the resistance of the occluder 100 entering the delivery sheath 50 becomes smaller, and the occluder 100 may smoothly enter the delivery sheath 50 with a smaller specification and is pushed in the delivery sheath 50 so that the pushing process is smoother and more successful. In addition, it is easy for the occluder to come out of the sheath due to the reduced resistance so that sudden shaking and trembling of the occluder may be prevented when coming out of the sheath due to the sudden increase of unsheathing force and poor control of strength, avoiding the excessive stimulation to the human body or damage to other tissues of the human body and improving the controllability and safety of the operation. Further, since the recess 401a of the woven main body 10a is provided, the recess is formed on a disc surface facing the blood flow to slow down an impact of the blood flow on the disc surface so that the occluder is more stably implanted at a defect site, and the endothelialization speed is increased.

Embodiment 2

Figure 10:
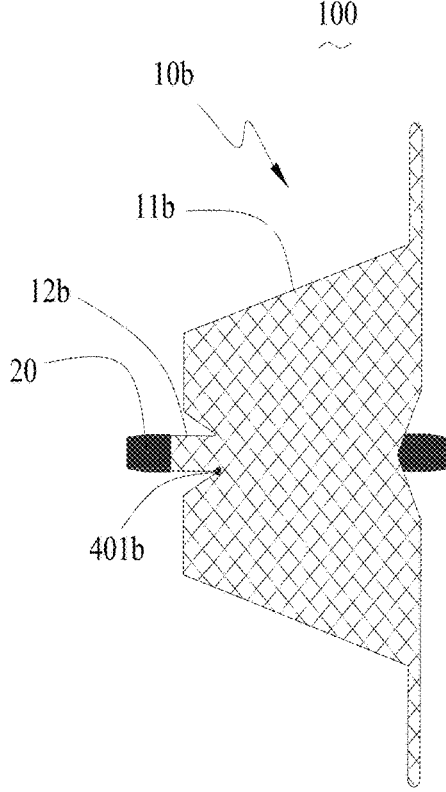
FIG. 10 is a schematic diagram of an occluder in a natural state according to embodiment 2 of the present invention.
Figure 11:
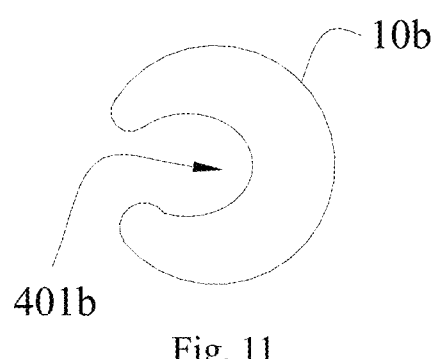
FIG. 11 is a schematic cross-sectional diagram of a woven mesh tube before being shaped according to embodiment 2 of the present invention.

As shown in FIGS. 10 and 11, in the embodiment, a woven main body 10b has a distal disc 11b and a shrinkage portion 12b connected to the distal disc 11b, and the radial cross-sectional dimension of the shrinkage portion 12b is smaller than the radial cross-sectional dimension of the distal disc 11b. A recess 401b is provided close to a transitional connection of the distal disc 11b and the shrinkage portion 12b. Alternatively, the recess 401b may be provided just at the transitional connection of the distal disc 11b and the shrinkage portion 12b.

In practical application, due to the large difference in the cross-sectional dimensions of the distal disc 11*b* and the shrinkage portion 12*b*, the resistance of entering the sheath generated at the transitional connection of the two is also correspondingly large. The transitional connection is also a position where the occluder is difficult to enter the sheath. The recess 401*b* is provided at or close to the transitional connection of the distal disc 11*b* and the shrinkage portion 12*b* so that the resistance of the woven main body 10*b* entering the sheath is greatly reduced, and entering and coming out of the sheath becomes smoother, thereby avoiding the difficulty of coming out of the sheath due to the difficulty of entering the sheath in the related art. Furthermore, sudden shaking and trembling of the occluder 100 may be prevented when coming out of the sheath due to the sudden increase of unsheathing force and poor control of strength, avoiding the excessive stimulation to the human body or damage to other tissues of the human body and improving the controllability and safety of the operation.

Embodiment 3

Figure 12:
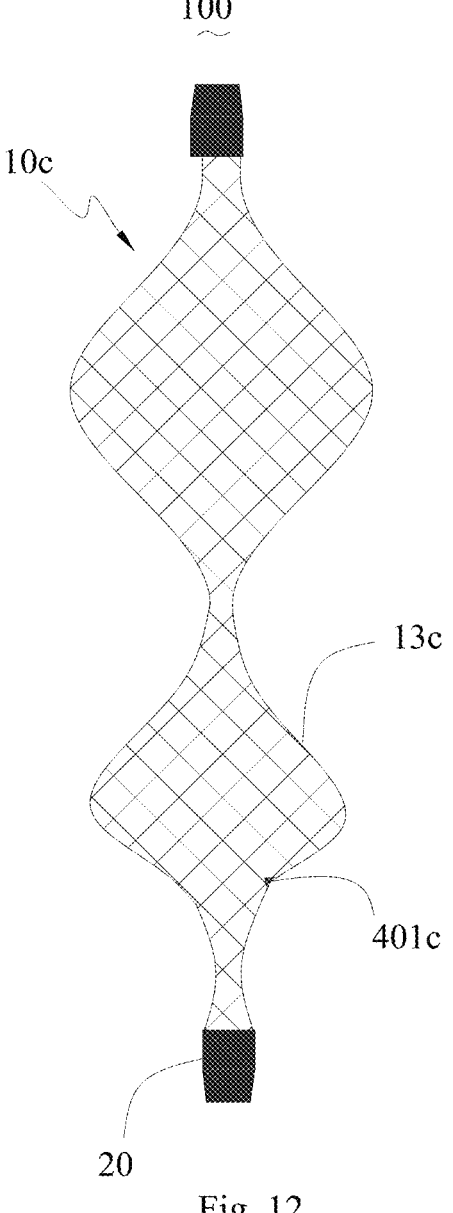
FIG. 12 is a schematic diagram of an occluder in a natural state according to embodiment 3 of the present invention.
Figure 13:
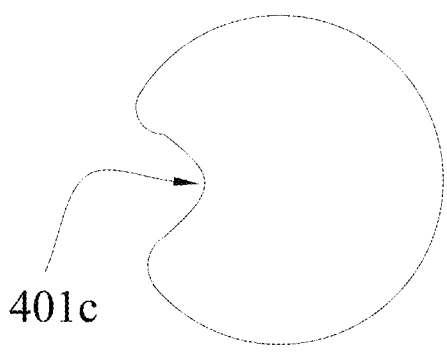
FIG. 13 is a schematic cross-sectional diagram of a woven mesh tube before being shaped according to embodiment 3 of the present invention.

Referring to FIGS. 12 and 13, in the embodiment, a woven main body 10*c* includes a proximal disc 13*c* at a proximal end, and a proximal bolt head 20 at a proximal end of the proximal disc 13*c*. In this embodiment, a recess 401*c* is provided between the proximal bolt head 20 and a disc surface of the proximal disc 13*c*, where the disc surface of the proximal disc 13*c* refers to a surface of the proximal disc 13*c* having the largest radial cross-sectional dimension. During the interventional operation, since there is a large difference in the radial dimensions of the proximal end of the occluder 100 and the disc surface of the proximal disc 13*c*, the cross-sectional diameter dimension of the woven main body 10*c* is gradually increased or abruptly increased from the proximal end of the occluder 100 to the disc surface of the proximal disc 13*c*. Therefore, a section from the proximal bolt head 20 to the disc surface of the proximal disc 13*c* is a position where the occluder 100 can find it difficult to enter the sheath. The recess 401*c* is provided between the proximal bolt head 20 and the disc surface of the proximal disc 13*c* so that the contact area between the woven main body 10*c* and the inner wall of the sheath may be reduced, thereby reducing the resistance of entering the sheath. Thus, the occluder 100 smoothly enters the sheath, improving the safety and operability of the operation and reducing the difficulty and risk of the operation.

Similarly, for the recess 401*c* in the embodiment, the position where the woven mesh tube needs to be provided with a recess may also be bounded and located correspondingly using a thin copper wire to form the woven mesh tube with the recess, and the cross-section thereof is as shown in FIG. 13. Then, the woven mesh tube is shaped, and after the shaping, the recess may be formed at a corresponding position of the woven main body 10*c*. Even if the thin copper wire is removed, the corresponding recess may still be maintained.

Embodiment 4

Figure 14:
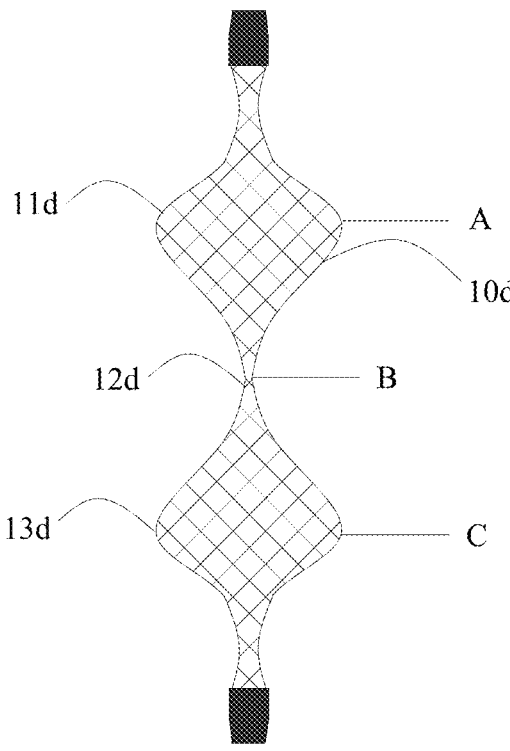
FIG. 14 is a schematic diagram of an occluder being stretched according to embodiment 4 of the present invention.
Figure 15:
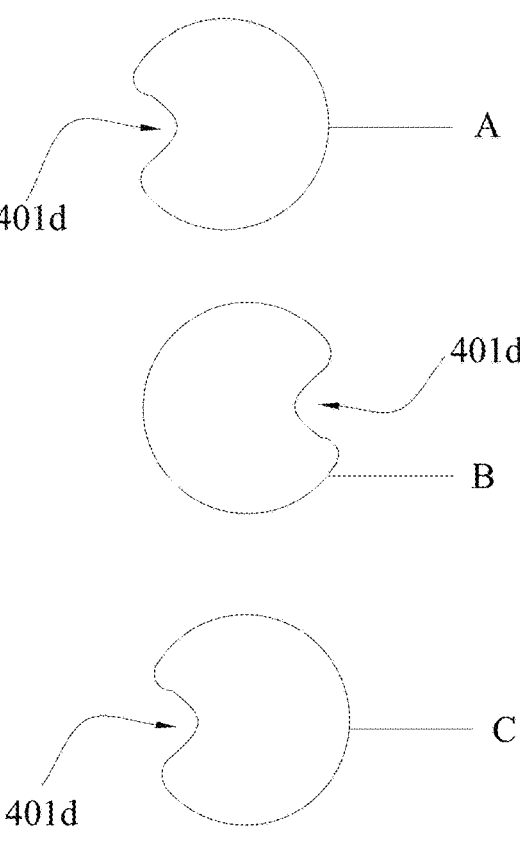
FIG. 15 is a schematic cross-sectional diagram of a woven mesh tube before being shaped according to embodiment 4 of the present invention.

Referring to FIGS. 14 and 15, the embodiment differs from the above-mentioned embodiments in that recesses 401*d* are provided at different positions. The recesses 401*d* are distributed along a side wall of a woven main body 10*d* in a spiral trajectory, and the woven main body 10*d* includes a distal disc 11*d*, a proximal disc 13*d*, and a waist portion 12*d* provided between the distal disc 11*d* and the proximal disc 13*d*. FIG. 15 provides schematic cross-sectional diagrams of the recesses 401*d* corresponding to three positions A, B, and C in FIG. 14. Namely, in this embodiment, the recesses 401*d* are spirally distributed around a central axis of the woven main body 10*d*. The recesses 401*d* are spirally distributed along the central axis to disperse the impact force of the blood flow and avoid stress concentration, thereby reducing the occurrence of wire fatigue fracture of the metal mesh tube. In the specific manufacturing, the side wall of the cylindrical woven mesh tube before shaping may be first processed using an auxiliary tool such as the thin copper wire to form recesses distributed along the side wall of the cylindrical woven mesh tube in a spiral trajectory and then shaped to form the woven main body.

Embodiment 5

Figure 16:
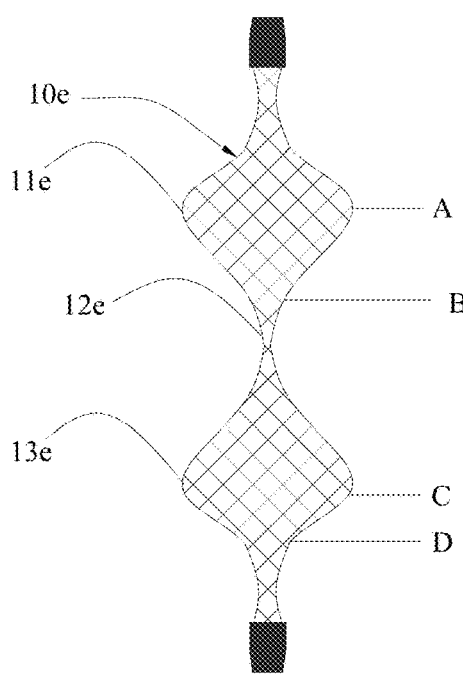
FIG. 16 is a schematic diagram of an occluder being stretched according to embodiment 5 of the present invention.
Figures 17, 18:
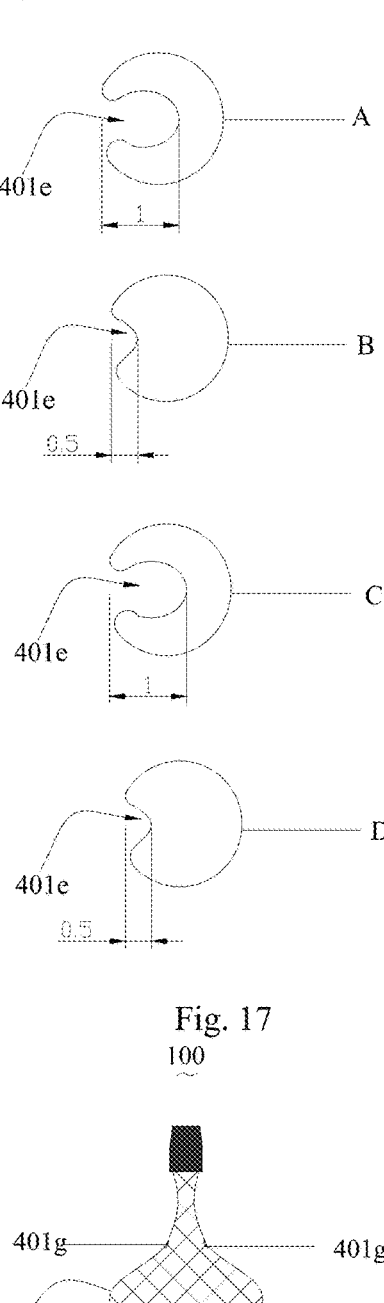
FIG. 17 is a schematic cross-sectional diagram of a woven mesh tube before being shaped according to embodiment 5 of the present invention.
FIG. 18 is a schematic diagram of an occluder being stretched according to embodiment 7 of the present invention.

Referring to FIGS. 16 and 17, in this embodiment, a woven main body 10*e* includes a distal disc 11*e*, a waist portion 12*e*, and a proximal disc 13*e*, and the waist portion 12*e* is provided between the distal disc 11*e* and the proximal disc 13*e*. Disc surface dimensions of the distal disc 11*e* and the proximal disc 13*e* are greater than the radial cross-sectional dimension of the waist portion 12*e*. A plurality of recesses 401*e* may be provided in the embodiment, and the recesses 401*e* are distributed on the woven main body 10*e* at intervals and have different depths. The depth of the recess on the distal disc 11*e* which is closer to the disc surface of the distal disc 11*e* is deeper, namely, the depth of the recess on the proximal disc 11*e* close to a longitudinal central axis of the proximal disc 11*e* is less than the depth of the recess away from the longitudinal central axis of the proximal disc 11*e*. For example, the depth of the recess 401*e* at a position A close to the disc surface of the distal disc 11*e* is 1 mm, and the depth of the recess 401*e* on the distal disc 11*e* at a position B away from the disc surface of the distal disc 11*e* is 0.5 mm, so the depth of the recess at the position A is greater than the depth of the recess at the position B. The depth of the recess on the proximal disc 13*e* which is closer to the disc surface of the proximal disc 13*e* is deeper, namely, the depth of the recess on the proximal disc 13*e* close to a longitudinal central axis of the proximal disc 13*e* is less than the depth of the recess away from the longitudinal central axis of the proximal disc 13*e*. For example, the depth of the recess 401*e* at a position C close to the disc surface of the proximal disc 13*e* is 1 mm, and the depth of the recess 401*e* on the proximal disc 13*e* at a position D away from the disc surface of the proximal disc 13*e* is 0.5 mm, so the depth of the recess at the position C is greater than the depth of the recess at the position D. Since the cross-sectional dimensions of the disc surface of the distal disc 11*e* and the disc surface of the proximal disc 13*e* are larger than those of other parts when the woven main body 10*e* enters the sheath, blocking or jamming occurs more easily closer to the disc surface of the distal disc 11*e* and the disc surface of the proximal disc 13*e* when entering the sheath. However, in this embodiment, the depth of the recess 401*e* close to the disc surface of the distal disc 11*e* and the disc surface of the proximal disc 13*e* is greater than the depth of the recess 401*e* away from the disc surface of the distal disc 11*e* and the disc surface of the proximal disc 13*e*, and a targeted arrangement is adopted so that most of the stress of the woven main body 10*e* close to the disc surface of the proximal disc 13*e* and the disc surface of the distal disc 11*e* when entering the sheath is toward a center of the woven main body 10*e*, thereby reducing a positive pressure between a side wall of the woven main body 10e and the inner wall of the sheath and reducing the resistance of entering the sheath.

A specific method for manufacturing the recess 401e in the embodiment may refer to the above-mentioned embodiment. The woven mesh tube is first located using a tool such as a thin copper wire to form the recess 401e, and then the shaping is performed, after the tool such as the thin copper wire is removed, the woven main body 10e having the recess 401e may be formed.

Embodiment 7

Figure 19:
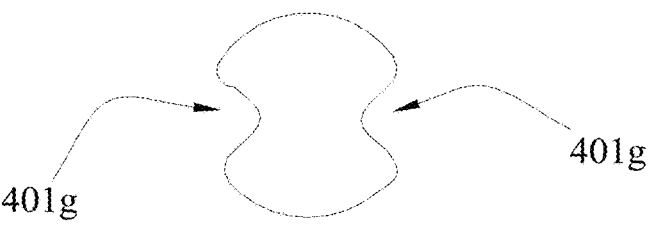
FIG. 19 is a schematic cross-sectional diagram of a woven mesh tube before being shaped according to embodiment 7 of the present invention.
Figure 20:
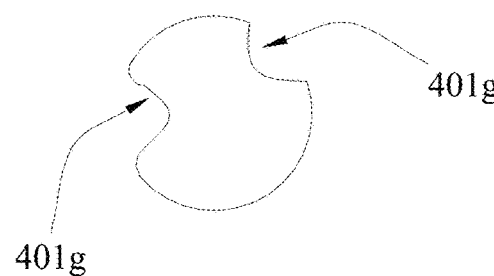
FIG. 20 is a schematic cross-sectional diagram of another woven mesh tube before being shaped according to embodiment 7 of the present invention.
Figure 22:
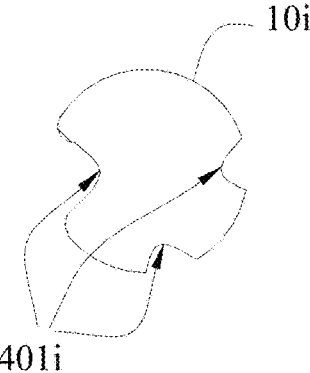
FIG. 22 is a schematic cross-sectional diagram of a woven mesh tube before being shaped according to embodiment 9 of the present invention.

Referring to FIGS. 18, 19, and 20, in the embodiment, as shown in FIG. 18, an even number of recesses 401g are provided, and the even number of the recesses 401g are provided in pairs on a side wall of a woven main body 10g, namely, any pair of the recesses 401g are provided symmetrically about a central axis of the woven main body 10g. This structure may make the stress distribution of the woven main body 10g of the occluder 100 more balanced when entering the sheath so that the resistance of entering the sheath may also be well reduced, thus reducing the difficulty and risk of the operation. When the paired recesses 401g are provided symmetrically, as shown in FIG. 19, the paired recesses 401g are positively symmetrical about the central axis of the woven main body 10g, namely, the paired recesses 401g are provided facing a center of the woven main body 10g, or as shown in FIG. 22, the paired recesses 401g are provided mirror-symmetrically away from the center of the woven main body 10g, namely, the recesses 401g are deviated from the center of the woven main body 10g without being aligned with it.

Embodiment 8

Figure 21:
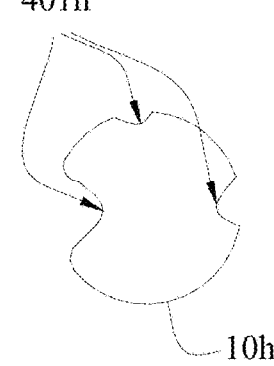
FIG. 21 is a schematic cross-sectional diagram of a woven mesh tube before being shaped according to embodiment 8 of the present invention.

In other embodiments, as shown in FIG. 21, a plurality of recesses 401h may be provided, each of the recesses 401h penetrates a woven mesh tube 10h along an axial direction, and the plurality of recesses 401h are asymmetrically provided on a side wall of the woven mesh tube 10h. This structure may also serve to reduce the radial stress abutting against the inner wall of the sheath when the occluder enters the pipe of the delivery sheath, thereby enabling the occluder to enter the sheath more smoothly, reducing the difficulty and risk of the operation.

Embodiment 9

As shown in FIG. 22, in other embodiments, a plurality of recesses 401i may be provided, and the recesses 401i are distributed on a side wall of a woven mesh tube 10i in a mesh point shape. At this time, when the shaped woven main body enters the sheath, the recesses 401i distributed in a mesh point shape may disperse and buffer the stress abutting against the inner wall of the sheath, thereby reducing the resistance of the occluder entering the sheath and enabling the occluder to enter the sheath more smoothly and successfully to reduce the difficulty and risk of the operation.

It should be noted that the method for processing and manufacturing the recesses 401g, 40h, and 40i in embodiments 7, 8, and 9 may refer to the method for manufacturing the recesses in other embodiments. Namely, the woven mesh tube is first bounded and located using a tool such as a thin copper wire to form a corresponding recess structure on the woven mesh tube, and then the shaping is performed to form the woven main body. The specific manufacturing method will not be repeated here.

For the small-sized occluder, due to its small size, the shrinkage deformation resistance reduction structure (recess) on the occluder is provided in a smaller size, so the shrinkage deformation resistance reduction structure (recess) is usually not visible through the naked eye. At this time, modeling measurement observation may be performed through a confocal microscope, and the difference is relatively obvious compared with the occluder of the same size without the shrinkage deformation resistance reduction structure (recess). In the following, the occluder without the shrinkage deformation resistance reduction structure of the related art and the occluder with the shrinkage deformation resistance reduction structure provided by the embodiment of the present invention having the same size are measured under the confocal microscope for comparison.

Figure 23:
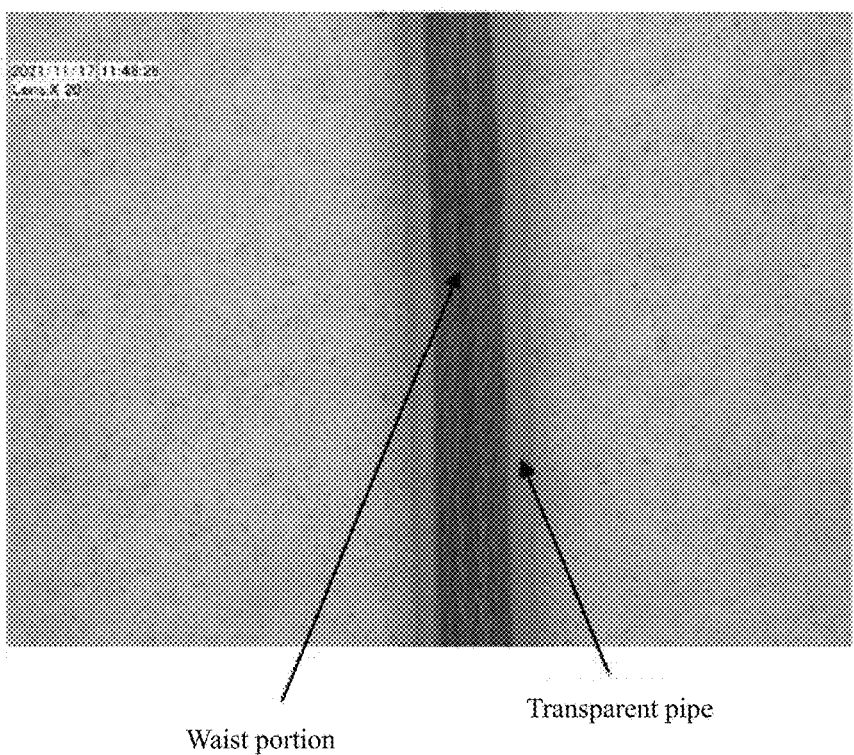
FIG. 23 is a related picture of an occluder without a shrinkage deformation resistance reduction structure of the related art in a transparent pipe according to the present invention.

FIG. 23 is a related picture of the occluder without the shrinkage deformation resistance reduction structure of the related art in a transparent pipe according to the present invention. In order to facilitate experimental observation, the occluder of the related art is pushed into the transparent pipe, and the inner diameter of the transparent pipe is equal to the inner diameter of the delivery sheath for delivering the occluder to simulate a use environment in which the occluder enters the delivery sheath during the interventional operation. Then the occluder is observed at the magnification of 20 to 100 times under an ordinary optical microscope. In the embodiment, the picture shown in FIG. 23 is observed at the magnification of 20 times.

Figure 24:
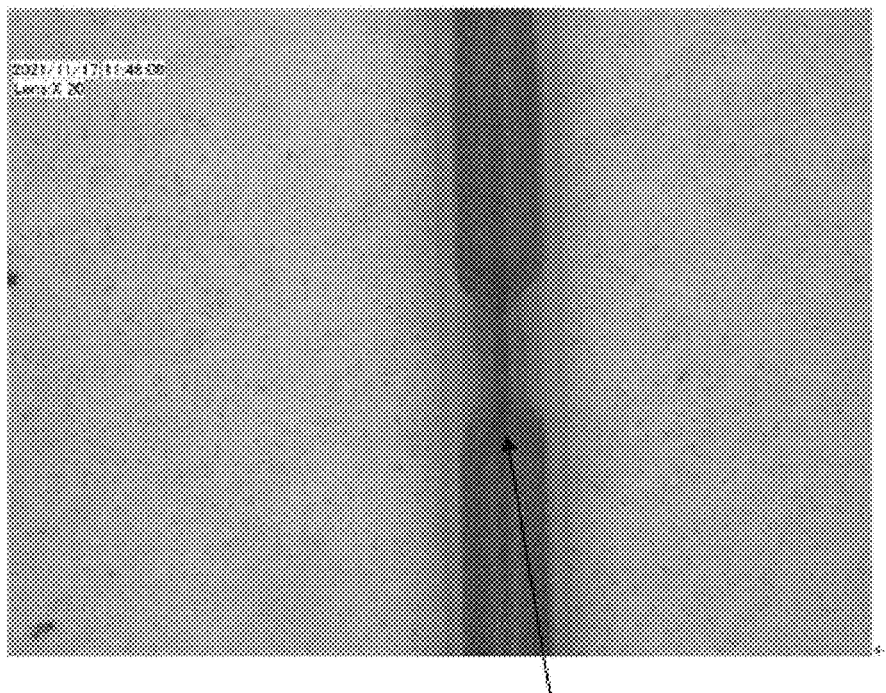
FIG. 24 is a related picture of an occluder with a shrinkage deformation resistance reduction structure in a transparent pipe according to an embodiment of the present invention.

The occluder with the shrinkage deformation resistance reduction structure (recess) provided at the waist portion is pushed into the transparent pipe, and the inner diameter of the transparent pipe is equal to the inner diameter of the delivery sheath for delivering the occluder to simulate the use environment in which the occluder enters the delivery sheath during the interventional operation. Then the occluder is observed at the magnification of 20 to 100 times under the ordinary optical microscope. In the embodiment, a picture shown in FIG. 24 is obtained by observing at the magnification of 20 times. Comparing FIG. 23 with FIG. 24, it can be seen that the occluder with the shrinkage deformation resistance reduction structure (recess) has obvious recesses at the waist portion when observed under the ordinary optical microscope, while the occluder without the shrinkage deformation resistance reduction structure (recess) has little change in the waist portion, and no obvious concave or recess is observed.

Figure 25:
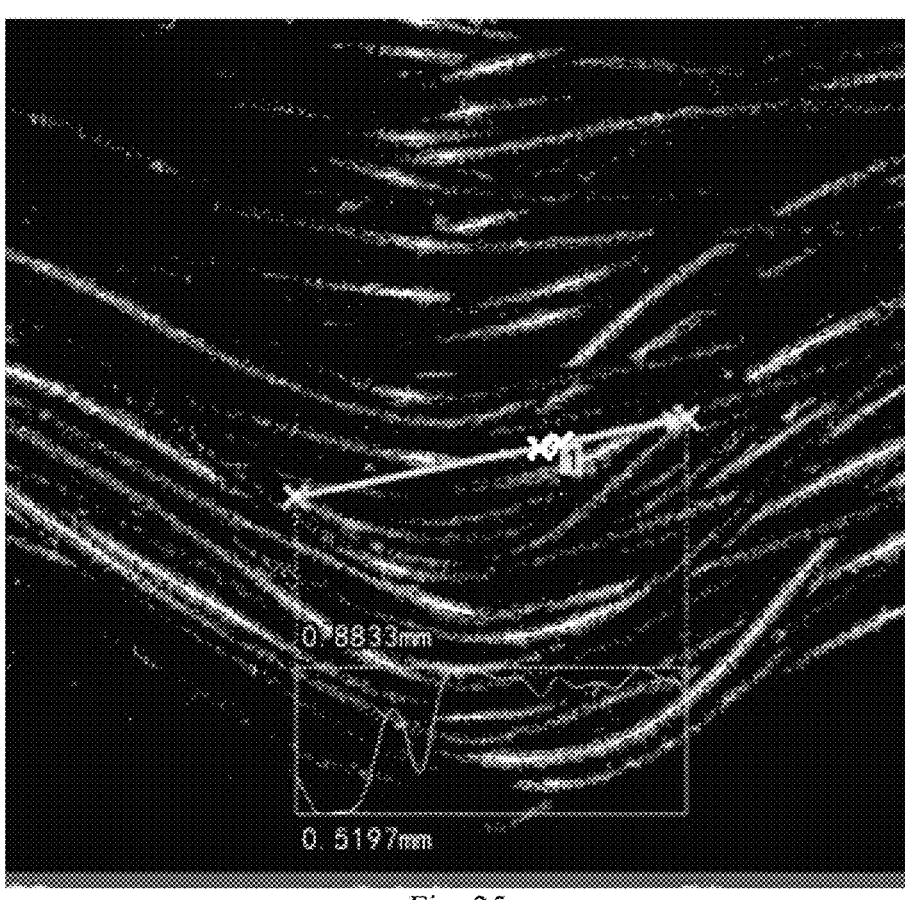
FIG. 25 is a related picture of quantitative measurement of a waist portion under a laser confocal microscope when an occluder without a shrinkage deformation resistance reduction structure of the related art is stretched according to the present invention.
Figure 27:
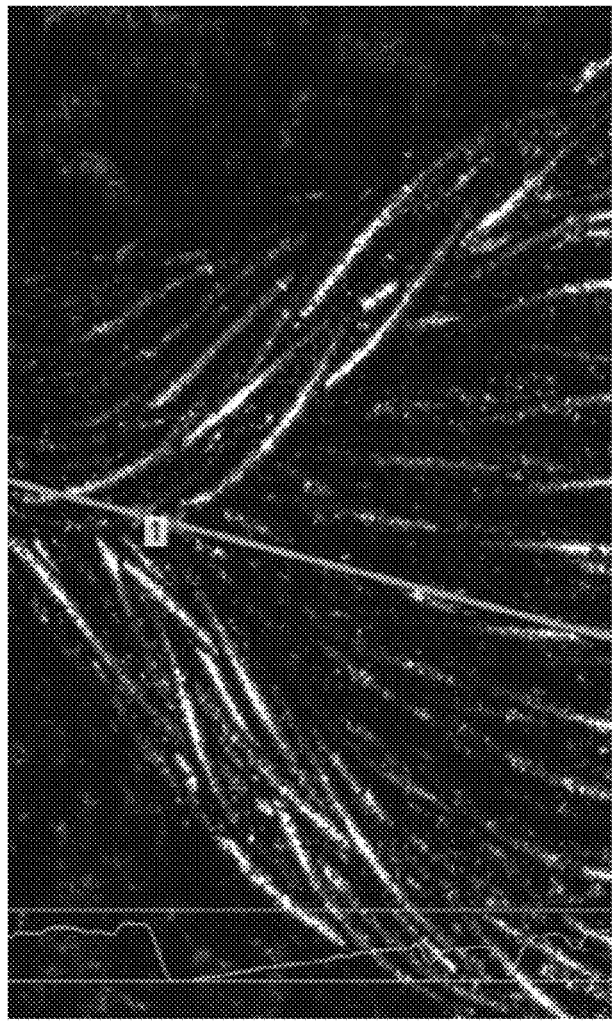
FIG. 27 is a related picture of quantitative measurement of a waist portion under a laser confocal microscope when an occluder with a shrinkage deformation resistance reduction structure is stretched according to an embodiment of the present invention.

FIG. 25 is a related picture of quantitatively measuring the depth of the recess of the waist portion under a laser confocal microscope when the occluder without the shrinkage deformation resistance reduction structure of the related art is in a natural state (namely, not subjected to an external force) according to the present invention. In the figure, no visible recess is seen in the waist portion of the occluder. However, FIG. 27 is a related picture of quantitatively measuring the depth of the recess of the waist portion under the laser confocal microscope when the occluder with the shrinkage deformation resistance reduction structure (recess) is in a natural state according to the embodiment of the present invention. In FIG. 27, a visible recess is seen in the waist portion.

Figure 26:
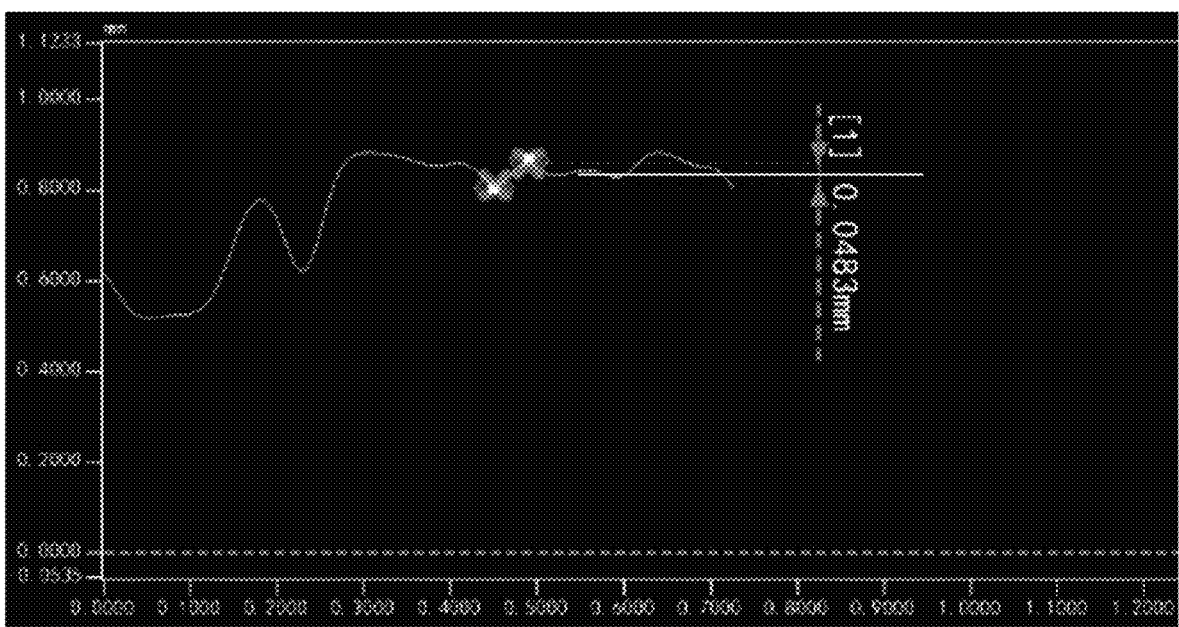
FIG. 26 is a measurement result graph of an occluder of FIG. 25 after being measured under a laser confocal microscope according to the present invention.
Figure 28:
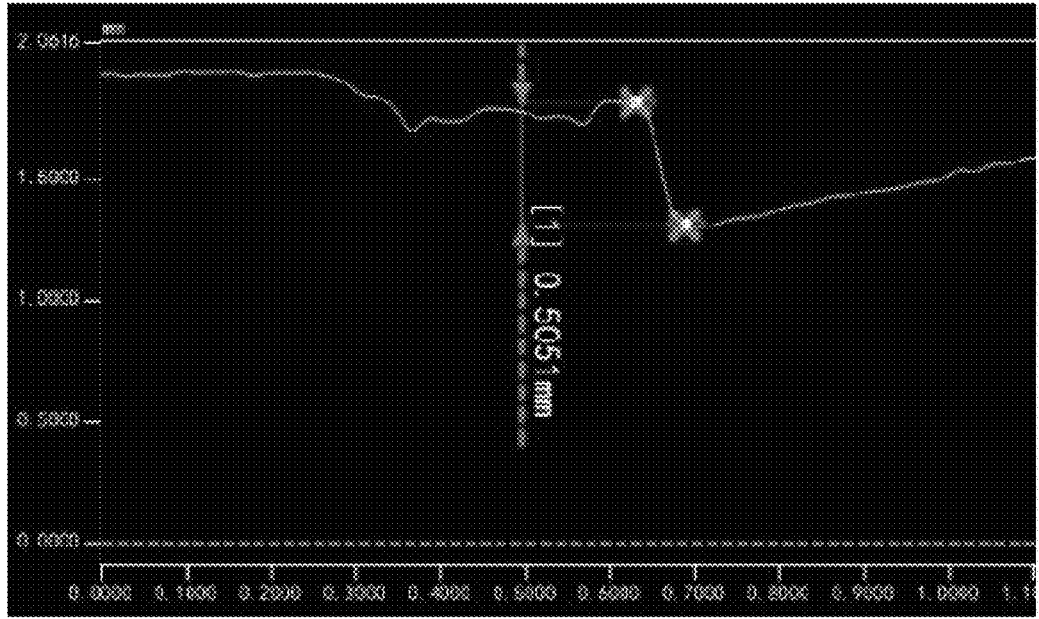
FIG. 28 is a measurement result graph of an occluder of FIG. 27 after measurement under a laser confocal microscope according to an embodiment of the present invention.

FIG. 26 is a result graph of the occluder of FIG. 25 after being measured at the magnification of 20 times under the laser confocal microscope according to the present invention. The abscissa represents a partial length of the occluder, and the ordinate represents a vertical depth of a corresponding position of the occluder. The depth difference is only 0.0483 mm since the waist portion of the occluder in this figure is not provided with the recess (namely, the shrinkage deformation resistance reduction structure). In this embodiment, the longitudinal central axis of the occluder is parallel to a stage plane of the microscope during measurement, the abscissa represents an axial length of the waist portion of the occluder in the natural state, and the ordinate represents a radial depth of a corresponding position of the waist portion of the occluder. It can be understood that if the shrinkage deformation resistance reduction structure is provided on an outer end surface of the disc surface, and the longitudinal central axis of the occluder is perpendicular to the stage plane of the microscope during measurement, the abscissa represents a radial length of the disc surface of the occluder in the natural state, and the ordinate represents an axial depth of a corresponding position of the disc surface of the occluder. FIG. 28 is a result graph of the occluder of FIG. 27 after being measured at the magnification of 20 times under the laser confocal microscope according to the embodiment of the present invention. The abscissa represents a partial length of the occluder, and the ordinate represents a radial width of a corresponding position of the occluder. The depth difference reaches 0.5051 mm since the waist portion of the occluder in this figure is provided with the recess (namely, the shrinkage deformation resistance reduction structure). It should be noted that if there is a measurement depth greater than 0.1 mm within the magnification range of 5 to 50 times of the laser confocal microscope, it is proved that the shrinkage deformation resistance reduction structure is purposely provided.

The modeling is performed using the confocal microscope, and the principle is to identify the depth of the position where the woven main body of the occluder is provided with the recess through measurement. In FIG. 27, the difference between the highest position and the lowest position of the recess on the woven main body of the occluder is 0.5051 mm, namely, the depth of the recess is 0.5051 mm, as shown in FIG. 28. However, since the woven main body of the occluder in the related art in a control group of FIG. 26 is not provided with the shrinkage deformation resistance reduction structure (recess), the depth at the waist portion of the occluder is only 0.0483 mm, and there is little height difference, which belongs to the error range of the process. The two groups have significant differences.

It should be noted that the occluder provided with the shrinkage deformation resistance reduction structure of the present invention is a single-layer occluder (namely, the proximal disc surface and the distal disc surface of the occluding disc of the occluder are both of single-layer woven structures), which may not be provided with a flow blocking membrane according to actual needs (for example, greater than or equal to 72 woven wires are used to form an occluder that may be loaded into a delivery sheath with an inner diameter of less than 6F), thus the inner diameter of the delivery sheath is reduced, and the trauma to the young patients is smaller.

The above are only preferred embodiments of the present invention and are not used to limit the present invention. Any modifications, equivalent substitutions, or improvements, etc., made within the spirit and principles of the present invention shall be included in the scope of the present invention.

The invention claimed is:

1. An occluder, comprising:
a woven main body, wherein the woven main body is formed by shaping a woven mesh tube formed by weaving woven wires having a shape memory function;
the woven main body is provided with a shrinkage deformation resistance reduction structure that reduces a resistance of the woven main body entering a sheath; the shrinkage deformation resistance reduction structure reduces the resistance of the woven main body entering the sheath by reducing the contact area between the woven main body and an inner wall of the sheath during radial shrinkage deformation of the woven main body entering the sheath.

2. The occluder according to claim 1, wherein the shrinkage deformation resistance reduction structure comprises a recess provided on the woven main body, and the recess is recessed toward an inner side of the woven main body.

3. The occluder according to claim 2, wherein at least one recess is provided, and the recess penetrates a proximal end and a distal end of the woven main body.

4. The occluder according to claim 3, wherein the recesses are distributed along a side wall of the woven mesh tube in a spiral trajectory.

5. The occluder according to claim 3, wherein a plurality of recesses is provided, each of the recesses penetrates the woven mesh tube along an axial direction, and the plurality of recesses are asymmetrically provided on a side wall of the woven mesh tube.

6. The occluder according to claim 2, wherein the woven main body comprises a distal disc and a shrinkage portion connected to the distal disc, and the radial cross-sectional dimension of the shrinkage portion is smaller than the radial cross-sectional dimension of the distal disc; the recess is close to a transitional connection of the distal disc and the shrinkage portion;
or,
the recess is provided at the transitional connection of the distal disc and the shrinkage portion.

7. The occluder according to claim 2, wherein the woven main body comprises a proximal disc at a proximal end and a proximal bolt head provided at a proximal end of the proximal disc; the recess is provided between the proximal bolt head and a disc surface of the proximal disc.

8. The occluder according to claim 2, wherein the woven main body comprises a distal disc, a proximal disc, and a waist portion connected between the proximal disc and the distal disc; disc surface dimensions of the distal disc and the proximal disc are greater than the radial cross-sectional dimension of the waist portion; a plurality of recesses are provided, and the plurality of recesses are distributed on the woven main body at intervals and have different depths; the depth of the recess on the proximal disc close to the longitudinal central axis of the proximal disc is less than the depth of the recess away from the longitudinal central axis of the proximal disc, and the depth of the recess on the distal disc close to the longitudinal central axis of the distal disc is less than the depth of the recess away from the longitudinal central axis of the distal disc.

9. The occluder according to claim 2, wherein an even number of the recesses are provided, and the even number of the recesses are provided in pairs on a side wall of the woven mesh tube; any pair of the recesses are provided symmetrically about the central axis of the woven mesh tube.

10. The occluder according to claim 2, wherein a plurality of recesses is provided, and the plurality of recesses is distributed on the woven mesh tube at intervals in a mesh point shape.

11. The occluder according to claim 1, wherein the occluder is of a single-layer structure without a flow blocking membrane structure.

12. The occluder according to claim 11, wherein the occluder is delivered through a sheath with an inner diameter of less than 6F.

13. An occluding system, comprising an occluder according to claim 1 and a delivery sheath configured to deliver the occluder.

\* \* \* \* \*